United States Patent
O'Mahony et al.

(10) Patent No.: US 10,676,712 B2
(45) Date of Patent: Jun. 9, 2020

(54) PROCESS FOR PRINTING 3D TISSUE CULTURE MODELS

(71) Applicant: Inventia Life Science Pty Ltd, Surry Hills, NSW (AU)

(72) Inventors: Aidan Patrick O'Mahony, Mascot (AU); Robert Hadinoto Utama, Earlwood (AU); Christopher Michael Fife, Kingswood (AU); Lakmali Atapattu, Lane Cove North (AU); Julio Cesar Caldeira Ribeiro, Waterloo (AU); Maria Kavallaris, Bondi Beach (AU); John Justin Gooding, Queens Park (AU)

(73) Assignee: Inventia Life Science Pty Ltd, Surry Hills, NSW (AU)

( * ) Notice: Subject to any disclaimer, the term of this patent is extended or adjusted under 35 U.S.C. 154(b) by 28 days.

(21) Appl. No.: 15/746,193

(22) PCT Filed: Jul. 21, 2016

(86) PCT No.: PCT/AU2016/000258
§ 371 (c)(1),
(2) Date: Jan. 19, 2018

(87) PCT Pub. No.: WO2017/011854
PCT Pub. Date: Jan. 26, 2017

(65) Prior Publication Data
US 2018/0230423 A1 Aug. 16, 2018

(30) Foreign Application Priority Data

Jul. 22, 2015 (AU) .................. 2015902917

(51) Int. Cl.
| | |
|---|---|
| *C12N 5/00* | (2006.01) |
| *G01N 33/50* | (2006.01) |
| *B29C 64/112* | (2017.01) |
| *B29C 64/40* | (2017.01) |
| *B29C 64/188* | (2017.01) |
| *B33Y 10/00* | (2015.01) |
| *B33Y 40/00* | (2020.01) |
| *B33Y 70/00* | (2020.01) |
| *A61L 27/52* | (2006.01) |
| *A61L 27/20* | (2006.01) |
| *B29L 31/40* | (2006.01) |

(52) U.S. Cl.
CPC ............ *C12N 5/0062* (2013.01); *A61L 27/20* (2013.01); *A61L 27/52* (2013.01); *B29C 64/112* (2017.08); *B29C 64/188* (2017.08); *B29C 64/40* (2017.08); *B33Y 40/00* (2014.12); *C12N 5/0012* (2013.01); *G01N 33/5082* (2013.01); *A61L 2300/62* (2013.01); *A61L 2300/64* (2013.01); *B29K 2005/00* (2013.01); *B29L 2031/40* (2013.01); *B33Y 10/00* (2014.12); *B33Y 70/00* (2014.12); *C12N 2503/02* (2013.01); *C12N 2513/00* (2013.01)

(58) Field of Classification Search
None
See application file for complete search history.

(56) References Cited

U.S. PATENT DOCUMENTS

| | | | | |
|---|---|---|---|---|
| 2004/0237822 A1* | 12/2004 | Boland | ................. | B01L 3/0268 101/483 |
| 2014/0221225 A1* | 8/2014 | Danen | ................ | G01N 33/5005 506/9 |
| 2015/0375453 A1* | 12/2015 | Yost | ..................... | B29V 64/386 435/174 |
| 2017/0319746 A1* | 11/2017 | Lutolf | ................ | A63B 53/0466 |

FOREIGN PATENT DOCUMENTS

WO 2015/017421 A2 2/2015

OTHER PUBLICATIONS

Mehesz (Scalable robotic biofabrication of tissue spheroids, 2011) (Year: 2011).*
Extended European Search Report issued in corresponding European Patent Application No. 16826915.7.
Faulkner-Jones et al., "Development of a valve-based cell printer for the formation of human embryonic stem cell spheroid aggregates", Biofabrication, 5(1), 015013, pp. 1-12 (2013).
Ferris et al., "Peptide modification of purified gellan gum", Journal of Materials Chemistry B, 3(6), pp. 1106-1115 (2015).
Marga et al., "Toward engineering functional organ modules by additive manufacturing", Biofabrication, 4(2), 022001, pp. 1-12 (2012).
Mironov et al., "Organ printing: Tissue spheroids as building blocks", Biomaterials, 30(12), pp. 2164-2174 (2009).
Pampaloni et al., "High-resolution deep imaging of live cellular spheroids with light-sheet-based fluorescence microscopy", Cell Tissue Res, 352(1), pp. 161-177 (2013).
Tan et al., "3D printing facilitated scaffold-free tissue unit fabrication", Biofabrication, 6(2), p. 024111, pp. 1-9 (2014).
Xu et al., "Study of Droplet Formation Process during Drop-on-Demand Inkjetting of Living Cell-Laden Bioink", Langmuir, 30(30), pp. 9130-9138 (2014).

(Continued)

*Primary Examiner* — Nghi V Nguyen
(74) *Attorney, Agent, or Firm* — Morgan, Lewis & Bockius LLP

(57) ABSTRACT

A process for producing a 3D tissue culture model by (a) printing a drop of bio-ink to a substrate; (b) printing a drop of activator to the drop of bio-ink to form a hydrogel droplet; (c) repeating steps (a) and (b) in any order to form a hydrogel mold adapted to receive a drop containing cells; (d) printing a drop containing cells to the hydrogel mold; and (e) repeating steps (a) and (b) in any order to form a 3D tissue culture model comprising the cells encapsulated in the hydrogel mold.

20 Claims, 2 Drawing Sheets

(56) References Cited

OTHER PUBLICATIONS

Wüst et al., "Controlled Positioning of Cells in Biomaterials—Approaches Towards 3D Tissue Printing", Journal of Functional Biomaterials, vol. 2, pp. 119-154 (2011).
Nagy Mehesz et al. "Scalable robotic biofabrication of tissue spheroids", Biofabrication, vol. 3(2), 025002 pp. 1-16 (2011).
International Search Report issued in corresponding International Patent Application No. PCT/AU2016/000258.
Extended European Search Report issued in corresponding European Patent Application No. 16826915.7, Search report dated Dec. 2, 2019.

\* cited by examiner

PROCESS FOR PRINTING 3D TISSUE CULTURE MODELS

RELATED APPLICATION

This application claims the benefit of Australian Provisional Patent Application No 2015902917, filed on 22 Jul. 2015, the disclosures of all of which are hereby expressly incorporated by reference in their entireties.

TECHNICAL FIELD

The technology relates to processes for forming three-dimensional tissue cultures such as 3D tissue culture models and uses in 3D tissue culture models.

BACKGROUND

Most cell structures in the human and animal body are organised in three-dimensions. This leads to complex intercellular interactions that cannot be mimicked in two-dimensional monolayers of cell cultures (Pampaloni, Ansari and Stelzer, 2013). However, two-dimensional cell culture has been the paradigm for typical in vitro cell culture. It has been demonstrated that cells behave more natively when cultured in three-dimensional environments but the formation of three-dimensional cell culture is difficult, expensive and laborious to generate.

Cellular spheroids are an example of a three-dimensional cell culture model and was among the first to be discovered and applied in basic research and clinical pharmacology. Cellular spheroids are aggregated cell clusters with a typical diameter of hundreds of microns. There are many techniques currently available for spheroid formation, such as the hanging drop method or rotational stirrers. Typically, culturing a cellular spheroid can take up to four days and has a 50% success rate.

Numerous studies have reported the printing of cells using drop-on-demand type technology. Faulkner-Jones et al. (2013) printed cells suspended in medium using the drop-on-demand method with a cell density of approximately $1\times10^5$ cells/ml in DMEM. Ferris et al. (2015) reported the printing of $2\times10^6$ cells/ml in bio-ink (gellan gum) using a commercially available inkjet printhead. Xu et al. (2014) reported the printing of cells in bio-ink at a density of $1\times10^7$ cells/ml. It was also reported that the most widely used cell concentrations in cell printing are between $10^5$ and $10^7$ cells/ml. While many previous studies describe printing of cells using drop-on-demand technology, there are no reports of printing a high cell density (greater than $10^7$ cells/ml) in bio-ink via the drop on demand method.

In order to form a cellular spheroid, for example, a high density of cells ($5\times10^7$–$2\times10^8$ cells/ml) must be aggregated into a small spherical cell cluster. The hanging drop technique achieves this by suspending droplets of culture medium containing isolated cells and allowing the cells to aggregate over three to seven days. Generating cellular spheroids using a drop-on-demand device presents difficulties due to the high viscosity associated with high cell densities and the small feature size in a drop-on-demand device. For this reason, in previous attempts to print tissue structures using spheroids, the cellular spheroids were firstly formed manually, loaded into a 3D printer and then printed to form a tissue structure. Tan et al. (2014) reported the 3D printing of preformed cellular spheroids via the extrusion method. Tan et al used a pressurised Pasteur pipette system as the droplet dispensing nozzle, which resulted in a continuous deposition of preformed spheroids. Marga et al. (2012) also reported the 3D printing of preformed spheroids via the extrusion method. In contrast, capillary micropipettes were used to contiguously arrange the cellular aggregates in a single line. Similarly, Mironov et al. (2009) also reported the 3D printing of preformed cellular spheroids via the extrusion method.

The present inventors have developed a process for preparing a 3D tissue culture model suitable for in vitro cell culture assays.

DISCLOSURE OF INVENTION

In a first aspect, there is provided a process for producing a 3D tissue culture model, the process comprising:
(a) printing a drop of bio-ink to a substrate;
(b) printing a drop of activator to the drop of bio-ink to form a hydrogel droplet;
(c) repeating steps (a) and (b) in any order to form a hydrogel mold adapted to receive a drop containing cells;
(d) printing a drop containing cells to the hydrogel mold; and
(e) repeating steps (a) and (b) in any order to form a 3D tissue culture model comprising the cells encapsulated in the hydrogel mold.

In an embodiment step (d) comprises printing a drop of cell-ink containing cells to the hydrogel mold.

In an embodiment step (d) comprises printing a drop of bio-ink containing cells to the hydrogel mold and printing a drop of activator to the drop of bio-ink containing cells before step (e).

In a second aspect, there is provided a process for producing a 3D tissue culture model, the process comprising:
(a) printing a drop of bio-ink to a substrate;
(b) printing a drop of activator to the drop of bio-ink to form a hydrogel droplet;
(c) repeating steps (a) and (b) in any order to form a hydrogel mold adapted to receive a drop containing cells;
(d) printing a drop of cell-ink containing cells to the hydrogel mold; and
(e) repeating steps (a) and (b) in any order to form a 3D tissue culture model comprising the cells encapsulated in the hydrogel mold.

In a third aspect, there is provided a process for producing a 3D tissue culture model, the process comprising:
(a) printing a drop of bio-ink to a substrate;
(b) printing a drop of activator to the drop of bio-ink to form a hydrogel droplet;
(c) repeating steps (a) and (b) in any order to form a hydrogel mold adapted to receive a drop containing cells;
(d) printing a drop of bio-ink containing cells to the hydrogel mold;
(e) printing a drop of activator to the drop of bio-ink containing cells; and
(f) repeating steps (a) and (b) in any order to form a 3D tissue culture model comprising the cells encapsulated in the hydrogel mold.

In an embodiment the process is carried out using a 3D bio-printer capable of forming drops. The 3D bio-printer is configured to print the bio-ink, activator, drops containing cells, drops of cell-ink containing cells in a manner that allows cell integrity, viability or functionality.

It will be appreciated that steps (a) and (b) can be carried out in any order. A drop of bio-ink can be applied to the substrate followed by a drop of activator to form the hydrogel droplet or a drop of activator can be applied to the substrate followed by a drop of bio-ink to form the hydrogel droplet.

In an embodiment the substrate is selected from any suitable vessel for containing, holding or growing cells. Examples include microtitre plate of different well configuration (6, 24, 48 and 96-well), microtitre plate with coverslip bottom of different well configuration (6, 24, 48 and 96-well), fluorodish of various sizes, chamber slides of different chamber configuration (1, 2, 4, 8 and 16), cover slip or microscope slides.

The bio-ink can be selected from any suitable material that is compatible with cells and can form a hydrogel when exposed to a suitable activator.

In an embodiment the bio-ink is a synthetic macromolecule, a polymer containing fructose, sucrose or glucose functionality, a non-ionic polymer, polyelectrolyte, or a natural macromolecule.

Examples include synthetic macromolecules such as polysaccharides; polymers containing fructose, sucrose or glucose functionality; polymer carrying amine-reactive functionalities such as aldehyde, epoxy, N-hydroxysuccinimide (NHS) or 2-vinyl-4,4-dimethylazlactone (VDM); polymer having thiol-reactive functionalities such as alkenes, alkynes, azides, halogens or cyanates; non-ionic polymer, such as poly(ethylene glycol) (PEG), poly(hydroxyethyl methacrylate (PHEMA), poly(ε-caprolactone) (PCL), poly(vinyl alcohol) (PVA), poly(NIPAAM) and poly(propylene fumarate) (PPF) and derivatives; polyelectrolyte—polymers that carry either positive or negative charge, amphoteric as well as zwitterionic polymer; polypeptide being a single linear chain of many amino acids (a minimum of 2 amino acids) held together by amide bonds. Natural macromolecules including polysaccharides, such as alginate, chitosan, hyaluronic acid, agarose and glycosaminoglycan; proteins, such as gelatin, fibrin, collagen, peptides or combinations thereof; or basement membrane extract.

Examples of reactive functionalities include amine-reactive functionalities such as aldehyde, epoxy, N-hydroxysuccinimide (NHS) or 2-vinyl-4,4-dimethylazlactone (VDM) and thiol-reactive functionalities such as alkenes, alkynes, azides, halogens or cyanates.

The activator is selected to form the bio-ink into a hydrogel.

In one embodiment the activator comprises inorganic salts, photoinitiators, polyelectrolyte, polypeptide, proteins and synthetic or natural macromolecules carrying amine or thiol groups.

In one embodiment the inorganic salts are barium chloride, calcium carbonate, calcium chloride, sodium chloride, magnesium sulphate or sodium hydroxide, the photoinitiators are 2,2-dimethoxy-2-phenylacetophenone (DMPA) and Irgacure.

In one embodiment the synthetic or natural macromolecules may naturally carry amine or thiol groups or may be synthetically modified.

In an embodiment the bio-ink may be chemically modified to introduce reactive functionalities.

In one embodiment the bio-ink is formed from alginate dissolved in calcium free Dulbecco's Modified Eagle Medium (DMEM), which may be supplemented with foetal calf serum (FCS) with dispersed neuroblastoma (SK-N-BE (2)) cells. In an embodiment the bio-ink is supplemented with about 1%, 2%, 3%, 4%, 5%, 6%, 5%, 8%, 9% or 10% FCS.

In one embodiment the activator is calcium chloride dissolved in MilliQ water.

The cell-ink can be selected from any suitable material that is compatible with the cells and keeps cells suspended during the printing process.

The cell-ink may be a buffer, cell culture medium or other material that allows integrity or viability of the cells.

In one embodiment the cell-ink materials include gellan gum, Ficoll™, dextran, glycerol, alginate, methylcellulose or poly(vinylpyrrolidone) (PVP).

In an embodiment the cell-ink is gellan gum in Phosphate Buffer Solution (PBS).

In an embodiment the cell-ink is Ficoll™ in PBS.

In an embodiment the cells are selected from mammalian liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, mesoderm-derived cells, or combinations thereof.

Additional cell types may include other mammalian cells (i.e. non-human), bacteria, fungi and yeast.

In an embodiment, the 3D tissue culture model contains further agents such as drug, therapeutic agent, antibody, small molecule inhibitor, kinase inhibitor, phosphatase inhibitor, antigen, pathogen, platelet, growth factor, cytokine, amino acids, nutrients (mono- and polysaccharides), conditioned media, antibiotic, antiviral, nanoparticle, RNA and relevant variants (e.g. siRNA, miRNA, etc).

In an embodiment the process is carried out using a 3D bio-printer capable of forming drops. The bio-printer having fluid reservoirs for at least bio-ink, activator, cell suspension and cleaning solution, a 3-axis motion control stage, a drop-on-demand droplet dispensing system, and pressure regulator to control pressure in the fluid reservoirs. The droplet dispensing system and 3-axis stage can be housed inside a sterile chamber such as a laminar flow cabinet. The printing platform can include adapters to print onto many kinds of substrate, such as micro-well plates and Petri dishes. The printing platform can be heated to 37° C. to assist cell proliferation.

The 3D bio-printer can be controlled by a computer having software to define the printing format.

In embodiments the 3D tissue culture model can contain at least about 100, 1000, 5000, 10000, 50000, 100000, 150000, 200000, 250000, 300000, 350000, 400000, 450000, or 500000 or more cells. It will be appreciated that other numbers of cells can be used.

Cell concentrations of up to about $450 \times 10^6$ cells/ml can be used in the 3D tissue culture models. It will be appreciated that even higher concentrations of cells can be used.

In an embodiment more than one cell type can be printed in the drop. For example two or more cell types can be mixed and used to form the 3D tissue culture model.

In an embodiment the process is carried out to form a plurality of 3D tissue culture models on the substrate. For example a 96-well microtitre plate is a suitable substrate and can be used for multiple cell assays.

In an embodiment the process is carried out in a substantially sterile environment.

In an embodiment the process is carried out at a temperature up to about 37° C.

Culture media can be added to the 3D tissue culture models to maintain cell viability or encourage growth and cell division.

In an embodiment the process is automated.

In an embodiment the process further comprises incubating the cells encapsulated in the hydrogel mold under conditions to allow cell growth or maintenance or spheroid formation.

In an embodiment the incubation is at any suitable temperature and conditions suitable for cell growth and maintenance. For example incubation can be carried out at about 37° C. with about 5% $CO_2$ for at least 24 hours. It will be appreciated that the incubation can be carried out at any temperature and time duration that allows cell growth or maintenance or spheroid formation of the type of cell in the hydrogel mold.

In an embodiment the 3D tissue culture model is a cellular spheroid.

In an embodiment the hydrogel allows visual inspection of the cells in the 3D tissue culture model using a microscope, for example.

In use the 3D tissue culture model can allow movement of nutrients and test agents into and out of the hydrogel for cell studies.

In a fourth aspect, there is provided a 3D tissue culture model produced by the process according to the first aspect.

In a fifth aspect, there is provided a 3D tissue culture model comprising a drop of cells encapsulated in a hydrogel formed by a 3D bio-printer.

In a sixth aspect there is provided use of a 3D tissue culture model in a cell assay.

In an embodiment, the cell assay is selected from cell motility, cell migration, cell invasion, transendothelial migration, epithelial-mesenchymal transition, mesenchymal-epithelial transition, spheroid formation and growth, cell differentiation (more specific stem cell differentiation, monitoring of cell differentiation markers), cell death (more specific cell apoptosis; cell necrosis), cell autophagy, cell proliferation, cell metabolism, protein turnover, protein distribution and location, cell signalling and downstream events, drug efficacy, drug pharmacodynamics, drug mechanism of action, drug receptor-mediated transport, mechanisms of drug internalization, biomarker evaluation, cell-cell junctions, cell-cell signalling and downstream events, cell morphology, cell adhesion, gene expression, protein expression, cell homing, cell cycle regulation and control, cytokine release, insulin production, protein secretion and intracellular trafficking and transport, receptor-ligand binding, antibody binding, antibody specificity, protein phosphorylation, proteosomal function, enzyme function (more specific enzyme inhibition), immunomodulation, clonogenicity, oxidative stress, protein folding, cell cytoskeleton, organelle morphology and function (more specific, relating to, mitochondria, chloroplast, peroxisomes, secretory vesicles, vacuole, ribosomes, nuclei, lysosomes, cilia, endoplasmic reticulum, golgi), membrane transport, hypoxia, angiogenesis, wound healing, neurite (outgrowth or formation), kinase function, phosphatase function, lamellipodial formation and dynamics; focal contact/adhesion formation, dynamics and signalling; cell sensing, mechanotransduction.

An advantage of the process is that high concentrations of cells can be included in the tissue culture model.

An advantage of the process is that high cell viability can be achieved after printing.

Advantages of the process are that it can be inexpensive, repeatable and scalable.

DEFINITIONS

Throughout this specification, unless the context clearly requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term 'consisting of' means consisting only of.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

Unless the context requires otherwise or specifically stated to the contrary, integers, steps, or elements of the invention recited herein as singular integers, steps or elements clearly encompass both singular and plural forms of the recited integers, steps or elements.

In the context of the present specification the terms 'a' and 'an' are used to refer to one or more than one (i.e., at least one) of the grammatical object of the article. By way of example, reference to 'an element' means one element, or more than one element.

In the context of the present specification the term 'about' mean that reference to a figure or value is not to be taken as an absolute figure or value, but includes margins of variation above or below the figure or value in line with what a skilled person would understand according to the art, including within typical margins of error or instrument limitation. In other words, use of the term 'about' is understood to refer to a range or approximation that a person or skilled in the art would consider to be equivalent to a recited value in the context of achieving the same function or result.

Those skilled in the art will appreciate that the invention described herein is susceptible to variations and modifications other than those specifically described. It is to be understood that the invention includes all such variations and modifications. For the avoidance of doubt, the invention also includes all of the steps, features, and compounds referred to or indicated in this specification, individually or collectively, and any and all combinations of any two or more of said steps, features and compounds.

In order that the present invention may be more clearly understood, preferred embodiments will be described with reference to the following drawings and examples.

DESCRIPTION OF EMBODIMENTS

Figure 1:
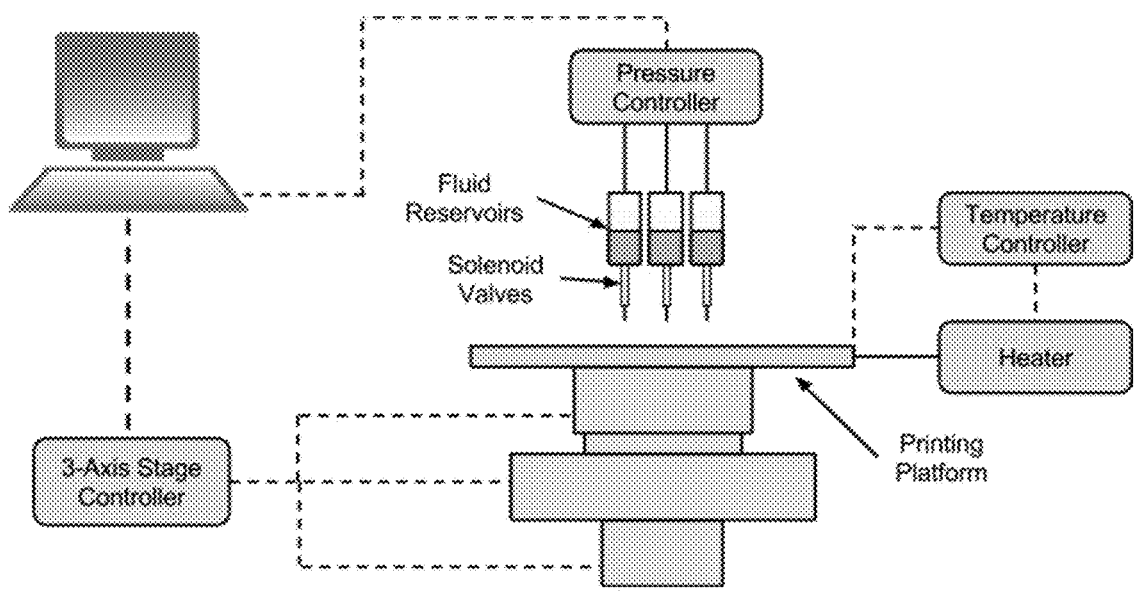
FIG. 1 shows a schematic of a 3D bio-printer.

Materials and Methods
Bio-Ink

In the present specification, bio-ink is defined as an aqueous solution of one or more types of macromolecule in which cells may be suspended or housed. Upon activation or crosslinking, it creates a hydrogel structure having its physical and chemical properties defined by chemical and physical composition of the bio-ink. Macromolecules are defined as an array of both synthetic and natural polymers, proteins and peptides. Macromolecules may be in their native state or chemically modified with amine or thiol-reactive functionalities.

Synthetic macromolecules may include:

Polysaccharides, such as polymers containing fructose, sucrose or glucose functionalities.

Non-ionic polymers, such as poly(ethylene glycol) (PEG), poly(hydroxyethyl methacrylate (PHEMA), poly(ε-caprolactone) (PCL), poly(vinyl alcohol) (PVA), poly(vinylpyrrolidone) (PVP), poly(NIPAAM) and poly(propylene fumarate) (PPF) and derivatives Polyelectrolytes—polymers that carry either positive or negative charge, amphoteric as well as zwitterionic polymer Polypeptides—a single linear chain of many amino acids (a minimum of 2 amino acids), held together by amide bonds Nucleobase containing synthetic polymers—polymers with nucleobase (adenine, thymine, guanine or cytosine) repeating units Natural macromolecules may include:

Polysaccharides, such as alginate, chitosan, gellan gum, hyaluronic acid, agarose and glycosaminoglycan Proteins, such as gelatin, fibrin and collagen DNA and Oligonucleotides, such as single stranded DNA (ssDNA), double stranded DNA (dsDNA) DNAzymes and Aptamers Basement membrane extracts Amine-reactive functionalities may include: aldehyde, epoxy, N-hydroxysuccinimide (NHS) and 2-vinyl-4,4-dimethylazlactone (VDM).

Thiol-reactive functionalities may include: alkenes, alkynes, azides, halogens and cyanates.

The bio-ink used and found suitable was alginate (at 2 w/v %) dissolved in calcium free DMEM supplemented with 10 v/v % FCS, L-glutamine and sodium pyruvate.

Bio-ink with dispersed SK-N-BE(2) neuroblastoma cells is referred to as bio-ink containing cells.

Activator

Activator is an aqueous solution comprising of either small molecules or macromolecules which interact with the bio-ink to form a hydrogel structure. The composition of the activator can be altered to control the physical properties of the resulting hydrogel. The type of activator used is highly dependent on the macromolecules used as well as the intended crosslinking process.

Activators can be selected from:

Inorganic salts such as calcium carbonate, calcium chloride, sodium chloride, magnesium sulphate. sodium hydroxide and barium chloride.

Photoinitiators such as 2,2-dimethoxy-2-phenylacetophenone (DMPA) and Irgacure.

Polyelectrolytes—polymers that carry an opposite charge to the macromolecules in the bio-ink. It could be cationic, anionic, amphoteric and zwitterionic Polypeptides—a single linear chain of many amino acids (a minimum of 2 amino acids), held together by amide bonds DNA linker—macromolecules carrying nucleotides or DNA sequences which complement those present on the bio-ink's macromolecules Natural or synthetic macromolecules carrying amine or thiol groups, either natively or through chemical modifications.

The activator used for the alginate bio-ink was calcium chloride at 4 w/v % dissolved in MilliQ water Crosslinking or Gelation This is the process whereby individual macromolecular chains are linked together by the activator to form a hydrogel. The crosslinking process can be classified to either chemical or physical crosslinking. Physical crosslinking or non-covalent crosslinking may include:

Ionic crosslinking—crosslinking via the interaction of the opposite charges present in the macromolecule and the activator. The activator may include charged oligomers, ionic salt and ionic molecule Hydrogen bonds—crosslinking via the electrostatic attractions of polar molecules. In this case, the macromolecule and the activator are carrying polar functionalities Temperature crosslinking—crosslinking via the rearrangement of the macromolecular chains as a response to change in temperature (heating or cooling).

Hydrophobic interaction or van der Waals force.

Chemical or covalent crosslinking involves chemical reactions between the macromolecule and the activator. The type of reactions may include:

Photocrosslinking whereby the crosslinking reaction is promoted by UV or light irradiation Michael-type addition reaction between thiols and vinyl-carrying macromolecules in aqueous media Schiff base reaction between amino and aldehyde groups Diels-alder reaction Click chemistry Aminolysis reaction to active ester group Enzyme crosslinking Examples of other bio-ink and activator combinations are set out in the Table below:

| Bio-Ink | Activator |
| --- | --- |
| Positively charged polyelectrolyte (e.g. poly(trimethylammonium) or poly(guanidium) | Negatively charged polyelectrolyte (e.g. poly(sulfonate), poly(carboxylic acid) |
| Fluorenylmethoxycarbonyl (Fmoc) polypeptide | Phosphate buffer solution Cell culture medium |
| Thiol-reactive macromolecules (e.g. PEG-diacrylate, hyaluronic acid maleimide) | Photoinitiator and/or thiol-containing macromolecules (e.g. bis-thiol-PEG) Thiol-containing polypeptides (e.g. bis-cysteine functionalised peptide) |
| Amine-reactive macromolecules (e.g. PEG-co-Poly(benzaldehyde), aldehyde-alginate | Amine-containing polypeptides (e.g. bis-amine functionalised peptide, gelatin, collagen) |
| Charged polysaccharides(e.g. alginate and gellan gum) | Inorganic salts (e.g. calcium chloride, barium chloride). |
| Macromolecules containing nucleobase (e.g. Adenine) | Macromolecules containing the corresponding nucleobase pair (e.g. Thymine) |

Cell-Ink

Cell-ink is an aqueous solution of one or more type of molecules or macromolecules in which cells are to be and remain evenly suspended throughout the 3D bio-printing process. The concentration of the cell-ink is optimised to prevent cells from settling but still maintains high cell viability.

Cell-link can be selected from:

Small molecules such as glycerol.

Macromolecules such as Ficoll™, dextran, alginate, gellan gum, methylcellulose and poly(vinylpyrrolidone) (PVP).

Ficoll™ is a neutral, highly branched, high-mass, hydrophilic polysaccharide which dissolves readily in aqueous solutions. Ficoll™ radii range from 2-7 nm and is prepared by reaction of the polysaccharide with epichlorohydrin. Ficoll™ is a registered trademark owned by GE Healthcare companies.

The cell-ink used was Ficoll™ 400 (at 10 w/v %) dissolved in PBS.

Cell-ink with dispersed SK-N-BE(2) neuroblastoma cells is referred to as cell-ink containing cells.

Gellan gum is a water-soluble anionic polysaccharide produced by the bacterium *Sphingomonas elodea* (formerly *Pseudomonas elodea*).

Cell-Culture Solutions

Cell-culture solutions are liquids that come into contact with the cultured cells and are suitable for various cell-related works. The preparation process includes careful analysis of the salt and pH balance, incorporation of only biocompatible molecules and sterilisation.

Some of the cell culture solutions include:

Cell culture medium such as Dulbecco's Modified Eagle Medium (DMEM), Minimum Essential Media (MEM), Iscove's Modified Dulbecco's Medium (IMDM), Media 199, Ham's F10, Ham's F12, McCoy's 5A and Roswell Park Memorial Institute (RPMI) medium Growth supplements such as foetal calf serum (FCS), epidermal growth factor (EGF), basic fibroblast growth factor (bFBF), fibroblast growth factor (FBF), endothelial cell growth factor (ECGF), insulin-like growth factor 1 (IGF-1) and platelet-derived growth factor (PDGF)

Biological buffers such as PBS, HEPES and CHES

Chelating and stabilizing solutions

Sterilized MilliQ water

Cell-Culture Conditions

Cells and the 3D tissue culture models can be incubated, cultured and maintained using standard cell culture techniques. The 3D tissue culture models comprising the cells encapsulated in the hydrogel mold can be incubated under conditions to allow or maintain cell growth or spheroid formation. Incubation is typically carried out at about 37° C. with a $CO_2$ level of 5% for at least 24 hours for most animal and human cell lines. It will be appreciated that incubation can be carried out at any suitable conditions, temperature and time duration that allows growth, maintenance or spheroid formation of the type of cell or cells in the hydrogel mold.

Utility Solutions

Utility solutions are defined as the solutions which do not come into contact with the cells but are used to clean and sterilise all printer surfaces exposed to the cells. These solutions may include:

Ethanol at the correct concentration

Sterile MilliQ water

Cell culture medium

Detergent

Hydrogen peroxide solution (2 w/v % maximum concentration)

Printing Substrates

Printing substrates are biocompatible consumables used to enclose and culture the printed cellular structure. These substrates may include:

Microtitre plate of different well configurations (6, 24, 48 and 96-well)

Microtitre plate with coverslip bottom of different well configurations (6, 24, 48 and 96-well)

Coverslips and microscope slides

Fluorodish of various sizes

Chamber slides of different chamber configurations (1, 2, 4, 8 and 16)

3D Bio-Printing Platform

A schematic of the 3D bio-printer developed and assembled by Inventia Life Science is shown in FIG. 1. The components in the 3D bio-printer include a 3-axis motion control stage, a drop-on-demand droplet dispensing system and a pressure regulator to control pressure in the fluid reservoirs. The droplet dispensing system and 3-axis stage can be housed inside a sterile chamber such as a laminar flow cabinet. The printing platform includes adapters to print onto many kinds of substrate, such as micro-well plates and Petri dishes. The printing platform can be heated to 37° C. to assist cell proliferation.

The 3-axis motion control stage is capable of accurately positioning the droplet dispensing system at a resolution of 10 μm in all three (X, Y and Z) dimensions. The four droplet dispensing systems consist of a solenoid valve with a jewelled orifice dispensing nozzle controlled by a microcontroller. The internal diameter of the jewelled orifice nozzle can be between 127 and 254 μm depending on the fluid viscosity and the desired droplet volume. Each droplet dispensing system is attached to a static pressure reservoir for the bio-ink and activator solutions to be dispensed via flexible tubing. The desired droplet volume can also be adjusted using the backpressure in the fluid reservoir and the solenoid valve open time. Typically, the backpressure is set to a pressure between 1 and 60 psi, the solenoid valve open time is 0.3 ms or greater and the droplet volume is between 1 and 500 nl. Flexible tubing connecting the bio-ink and activator reservoirs were kept as short as possible in order to minimize the amount of time it would take to prime the system and to purge it at the end of a printing routine.

Control Software

The 3D bio-printer is controlled via custom software developed for printing biological assays. The software includes a graphical user interface (GUI). Through the GUI the end user can select different assay printing routines and change the assay parameters, such as droplet spacing and droplet volume. The user can also manually control the spatial position of the droplet dispensing system and create a custom pattern of droplets. Additional features of the software include routines for priming and purging the droplet dispensing system.

Preparation of Bio-Ink

Initially, bio-ink is prepared by mixing the right type and amount of macromolecules in the appropriate cell-culture solution. After achieving homogeneity, the blank bio-ink is sterilised via both UV irradiation and filtration (0.22 μm filter). The bio-ink is then kept at 4° C. until further usage.

Preparation of Cells

Harvest cells by washing with PBS. Aspirate PBS. Add trypsin and incubate at 37° C. to dissociate cells from flask surface. Add tissue culture media to collect dissociated cells into a tube. Centrifuge cells, aspirate supernatant and resuspend pellet in fresh media. Perform cell count by mixing equal volumes of cell suspension and trypan blue stain. Perform calculation to determine the cell concentration. Desired numbers of cells then can be added to bio-ink, cell-ink or added to cell culture solutions.

Preparation of Activators

The correct type and amount of molecules were dissolved in the appropriate cell-culture solution. The resulting solution was sterilised via UV irradiation and filtration prior to use.

Preparation of Cell-Ink

The correct type and amount of molecules were dissolved in the appropriate cell-culture solution. After achieving homogeneity, the resulting solution was sterilised via UV irradiation and filtration prior to use. The cell-ink was then kept at room temperature until further use.

Preparation of 3D Bio-Printer

The printing cartridge containing the working fluids is loaded into the 3D bio-printer via a connection. Prior to commencing a printing routine, the droplet dispensing system and connecting fluidic channels are sterilized with ethanol, water, media and air. After sterilization the droplet dispensing system is primed and air bubbles are cleared from the fluidic system.

Cell Harvesting

Cultured cells of interest at certain confluency are harvested by following the already established protocols. To make up the bio-ink or cell-ink containing cells, harvested cells are resuspended at the correct cell concentration to give $2.5 \times 10^8$ cells/ml concentration in 200 µl of bio-ink or cell-ink. The resulting cell pellets are then redispersed in the correct volume of bio-ink or cell-ink. The bio-ink or cell-ink containing cells is then ready for use in the 3D bio-printer.

Preparation of the Printing Cartridge

In a sterile environment, the activator, bio-ink and bio-ink or cell-ink containing cells are slowly loaded into the appropriate cartridge vials using a micropipette to avoid the generation of small bubbles. The cartridge is then closed to maintain its sterility and loaded into the printer for the printing process.

Printing of Hydrogel Mold

Figure 2:
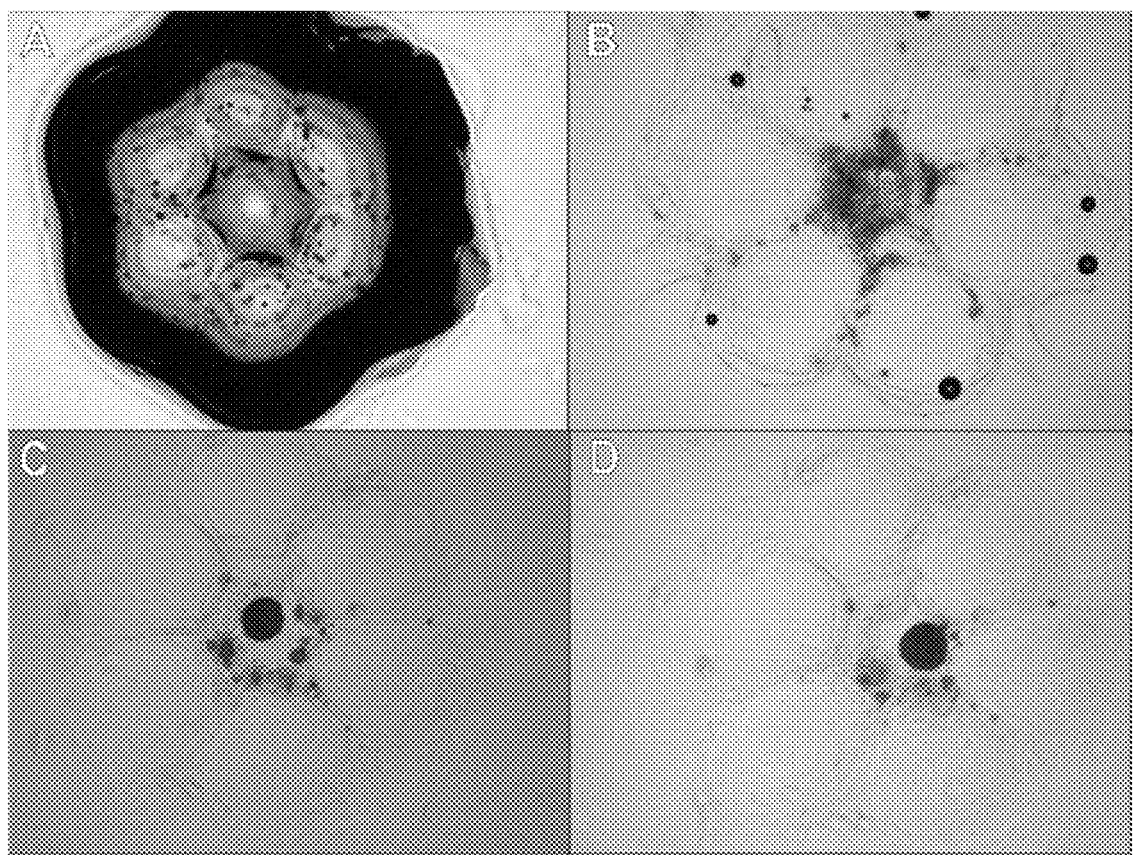
FIG. 2 shows example of printed hydrogel mold with cells colonies printed inside. A: printed hydrogel mold with cup at centre; B: cells printed into cup at centre of hydrogel mold; C: cell spheroid formed after incubation for 48 hours; D: cells spheroid formed after 72 hours incubation.

The hydrogel mold was printed using a drop-on-drop process whereby a droplet of bio-ink and a droplet of activator were deposited on top of each other to produce a hydrogel. This process can be repeated and used to form 3D hydrogel structures by building up layers of hydrogel. An example of a printed hydrogel mold with cells printed in the centre is shown in FIG. 2.

Cell Types 3D tissue culture models such as spheroids can be prepared from any suitable cell type including adherent cells such as mammalian liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, mesoderm-derived cells, or combinations thereof.

Additional cell types may include other eukaryotic cells (e.g. chinese hamster ovary), bacteria (e.g. *Helicobacter pylori*), fungi (e.g. *Penicillium chrysogenum*) and yeast (e.g. *Saccharomyces cerevisiae*).

The cell line SK-N-BE(2) (neuroblastoma cells) has been used successfully in the process to produce 3D tissue culture models under a range of conditions. It will be appreciated that other cell lines would be expected to perform as required in 3D tissue models produced by the process developed. Other cell lines used include DAOY (human medulloblastoma cancer cells), H460 (human non-small lung cancer) and $p53^{R127H}$ (human pancreatic cancer cells). Other cell lines that may be suitable are listed on 088 and 089.

3D bio-printing technology was developed to produce high density 3D tissue culture models encapsulated in a hydrogel mold via drop-on-demand techniques. Specifically, a 3D printing technology was used to print biocompatible hydrogel molds using a bio-ink and activator that are constructed in a layer-by-layer manner to fabricate a variety of 3D structures. During the fabrication of the hydrogel molds, high cell density droplets can be included into the hydrogel mold.

EXAMPLES

Example 1

Materials and Methods

Alginate (high >55% guluronic acid content, 50,000-80,000 g/mol, FMC Biopolymer), calcium chloride (BioReagent, Sigma Aldrich), phosphate buffered solution without calcium chloride (PBS, Gibco), Dulbecco's modified eagle medium (DMEM, Gibco), calcium free DMEM (Gibco), sodium pyruvate (Gibco), L-glutamine (Gibco), Gellan gum (Sigma Aldrich), trypsin (Sigma Aldrich), 0.22 µm syringe filter (polyethersulfone membrane, Merck Millipore), T150 flask (Corning), 15 ml centrifuge tube (Corning), ethanol (Sigma Aldrich), were used as received. Tissue culture media was made by mixing DMEM with FCS at 10 v/v %.

Cell Type

SK-N-BE(2) neuroblastoma cells were used.

Cell Culture

Neuroblastoma at 80% confluency in a T150 flask was washed with 3 ml PBS. After aspiration of excess PBS, 3 ml of trypsin was added and the flask was incubated at 37° C. to dissociate cells from flask surface for 5 minutes. Subsequently, 7 ml of tissue culture media was added and the dissociated cells were transferred into a 15 mL tube. The cell dispersion was centrifuged at 400 g for 3 minutes. The supernatant was discarded and the cell pellet was resuspended in 5 ml of media. Cell counting was then conducted by mixing equal volumes of cell suspension and trypan blue stain to determine the cell concentration.

Substrate 6-well microtiter plate supplied by Corning incorporated was used as received. The sterile packaging was opened in a sterile environment to maintain the content sterility.

Bio-Ink

Sodium pyruvate (5.5 ml at 100 mM), FCS (55 ml) and L-glutamine (5.5 ml at 200 mM) was added to calcium free DMEM (500 ml) to create the bio-ink dispersant. Alginate (0.2 g) was added slowly into the dispersant (10 ml) under vigorous stirring to give the bio-ink at 2 w/v %. The resulting homogenous solution was then filtered through a 0.22 µm syringe filter under a sterile environment.

Activator

Calcium chloride (0.4 g) was dissolved in 10 ml MilliQ water to give 4 w/v %. The solution was then UV sterilised for 10 minutes and filtered through a 0.22 µm filter in a sterile environment.

Cell-Ink

Gellan gum (0.05 g) was dissolved in 10 ml warm PBS to give 0.5 w/v %". The solution was vortexed as it cools down to room temperature. The solution was then UV sterilised for 10 minutes and filtered through a 0.22 µm filter in a sterile environment.

Harvested neuroblastoma cells dispersed in DMEM at $10\times10^6$ cells/ml (5 ml) was centrifuged to give a cell pellet of $50\times10^6$ cells. The resulting pellet was then redispersed in the cell-ink (0.2 ml) to give a bio-ink solution with dispersed SK-N-BE(2) cells at $250\times10^6$ cells/ml.

Cell Printing Conditions

The printer was initially sterilised with ethanol (70 v/v % in water) wiping, air dried and placed inside a biosafety cabinet. The fluid lines and droplet dispensing systems were also sterilised using ethanol, water, sterile Milli-Q water and tissue culture media purging, in that order. The cell-ink containing cells, bio-ink and activator were then loaded into their respective vials. The droplet dispensing systems were then primed by purging air from the fluid supply lines prior to starting the printing routine.

The droplet dispensing system for each fluid used a different nozzle diameter and supply pressure in the reservoir. The nozzle diameter for the bio-ink, activator and cell-ink plus cells was 0.007", 0.003" and 0.007" respectively. The supply pressure for the bio-ink, activator and cell-ink plus cells was 40, 5 and 12 psi respectively.

The hydrogel mold comprised multiple layers of bio-ink and activator droplets in a cylindrical pattern as shown in FIG. 2. Each layer in the hydrogel mold was printed by depositing a droplet of bio-ink, then a droplet of activator directly on top or vice versa and repeating this process to form the cylindrical structure. After the first two layers bio-ink or activator were not deposited at the centre of the cylindrical structure leaving an indentation or cup at the centre of the structure. This process was repeated for multiple subsequent layers. One to five droplets of cell-ink containing cells were deposited into the centre or cup in the hydrogel mold. Finally, additional layers of hydrogel were printed in the same fashion to encapsulate the cells inside the hydrogel mold.

After printing was completed the microtiter plate was placed in an incubator (37° C. and 5% $CO^2$) for a period of 72 hours.

Cell Concentrations

Cell-ink with SK-N-BE(2) at $250\times10^6$ cells/ml was used in the experiment.

Cell Viability

Cell viability of greater than or equal to 95% was obtained.

Example 2

Hydrogel mold or cup was printed using bio-ink, cell-ink and activator, as detailed in Example 1, at a supply pressure of 40 psi, 12 psi and 5 psi respectively. SK-N-BE(2) cells in cell-ink were printed into centre of hydrogel cup at a concentration of 100 million cells/ml. Microscope images of the printed 3D cell culture model showed cell spheroid formation after incubation for 24, 48 and 120 hours.

Example 3

Hydrogel mold or cup was printed using bio-ink and activator, as detailed in Example 1, at a supply pressure of 40 psi and 5 psi respectively. The cell-ink was Ficoll™ (Sigma Aldrich, 1.65 g) dissolved in PBS (10 ml) to give 16.5 w/v %. SK-N-BE(2) cells in cell-ink were printed into centre of hydrogel cup at a concentration of 250 million cells/ml, at a supply pressure of 20 psi. Microscope images of the printed 3D cell culture model showed cell spheroid formation after incubation for 24, 48 and 72 hours.

Example 4

Hydrogel mold or cup was printed using bio-ink, cell-ink and activator, as detailed in example 3, at a supply pressure of 40 psi, 20 psi and 5 psi respectively. $p53^{R127H}$ cells in cell-ink were printed into centre of hydrogel cup at a concentration of 250 million cells/ml. Microscope images of printed model showed cell spheroid formation after incubation for 24, 48 and 72 hours.

Example 5

Hydrogel mold or cup was printed using bio-ink, cell-ink and activator, as detailed in Example 3, at a supply pressure of 40 psi and 5 psi respectively. The cell-ink was Ficoll™ (Sigma Aldrich, 1 g) dissolved in PBS (10 ml) to give 10 w/v %. $p53^{R127H}$ cells in cell-ink were printed into centre of hydrogel cup at a concentration of 250 million cells/ml, at a supply pressure of 20 psi. The mold encapsulating the drop of cells was incubated at 37° C. to allow cell growth and spheroid formation after incubation for 24 to 48 hours.

Example 6

Hydrogel mold or cup was printed using bio-ink, cell-ink and activator, as detailed in Example 5, at a supply pressure of 40 psi, 20 psi and 5 psi respectively. DAOY cells in cell-ink were printed into centre of hydrogel cup at a concentration of 250 million cells/ml. The mold encapsulating the drop of cells was incubated at 37° C. to allow cell growth and spheroid formation after incubation for 24 to 48 hours.

Example 7

Hydrogel mold or cup was printed using bio-ink, cell-ink and activator, as detailed in Example 5, at a supply pressure of 40 psi, 20 psi and 5 psi respectively. H460 cells in cell-ink were printed into centre of hydrogel cup at a concentration of 250 million cells/ml. The mold encapsulating the drop of cells was incubated at 37° C. to allow cell growth and spheroid formation after incubation for 24 to 48 hours.

Example 8

Hydrogel mold or cup was printed using bio-ink, cell-ink and activator, as detailed in Example 5, at a supply pressure of 40 psi, 20 psi and 5 psi respectively. SKOV-3 cells in cell-ink were printed into centre of hydrogel cup at a concentration of 250 million cells/ml. The mold encapsulating the drop of cells was incubated at 37° C. to allow cell growth and spheroid formation after incubation for 24 to 48 hours.

Applications

3D Tissue Culture Model Assay

Figure 3:
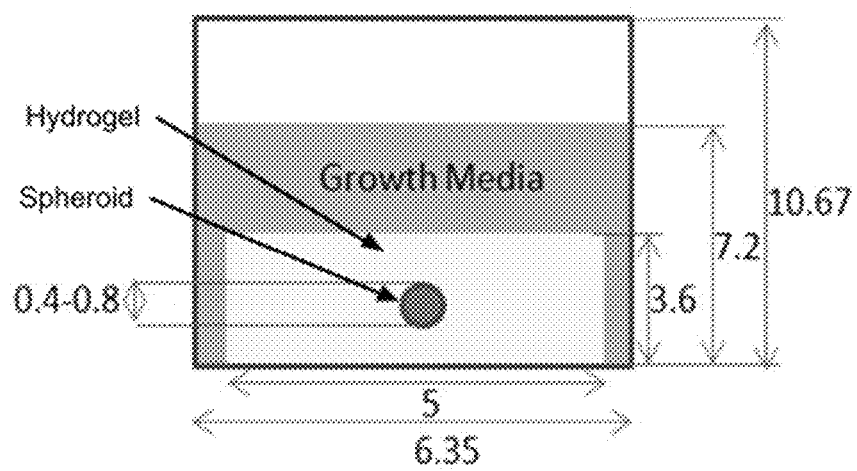
FIG. 3 shows a schematic of a 3D tissue culture model assay (dimensions in mm).

A 3D tissue culture model assay was constructed inside a well in a multi-well plate, for example a 96 well-plate. The first step was to print the bottom half of the cylindrical hydrogel structure or mold that will support the 3D tissue culture model. This is achieved using the drop-on-drop process with bio-ink and activator. The cell-ink droplet containing a high density of cells is then printed into the centre of the cylindrical hydrogel structure as shown in FIG. 3. The 3D tissue culture model was subsequently encapsulated in the hydrogel by further printing using the drop-on-drop process with bio-ink and activator. Finally, the printing process on a well is finished by the deposition of growth media with or without drug or other test agent (50, 100, 150 or 200 µl).

In Vitro Applications

Examination of biological phenotypes, including but not limited to, cell motility, cell migration, cell invasion, transendothelial migration, epithelial-mesenchymal transition, mesenchymal-epithelial transition, spheroid formation and growth, cell differentiation (more specific stem cell differentiation, monitoring of cell differentiation markers), cell death (more specific cell apoptosis; cell necrosis), cell autophagy, cell proliferation, cell metabolism, protein turnover, protein distribution and location, cell signalling and downstream events, drug efficacy, drug pharmacodynamics, drug mechanism of action, drug receptor-mediated transport, mechanisms of drug internalization, biomarker evaluation, cell-cell junctions, cell-cell signalling and downstream events, cell morphology, cell adhesion, gene expression, protein expression, cell homing, cell cycle regulation and control, cytokine release, insulin production, protein secretion and intracellular trafficking and transport, receptor-ligand binding, antibody binding, antibody specificity, protein phosphorylation, proteosomal function, enzyme function (more specific enzyme inhibition), immunomodulation, clonogenicity, oxidative stress, protein folding, cell cytoskeleton, organelle morphology and function (more specific, relating to, mitochondria, chloroplast, peroxisomes, secretory vesicles, vacuole, ribosomes, nuclei, lysosomes, cilia, endoplasmic reticulum, golgi), membrane transport, hypoxia, angiogenesis, wound healing, neurite (outgrowth or formation), kinase function, phosphatase function, lamellipodial formation and dynamics; focal contact/adhesion formation, dynamics and signalling; cell sensing, mechano-transduction.

List of substances that can be delivered or administered to cells, include but not limited to, drug, therapeutic agent, antibody, small molecule inhibitor, kinase inhibitor, phosphatase inhibitor, antigen, pathogen, platelet, growth factor, cytokine, amino acids, nutrients (mono- and poly-saccharides), conditioned media, antibiotic, antiviral, nanoparticle, RNA and relevant variants (e.g. siRNA, miRNA, etc).

Printing Structure Types

Printing of a structure that is partially composed of regions without cells and at least one region containing at least one spheroid.

Printing of a structure containing at least two spheroids, where different spheroids can either be comprised of the same or different cell type.

Printing of a structure containing adjacent spheroids, where adjacent spheroids can either be the same or different cell type.

Printing of a structure containing at least one of the substances listed in above.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Faulkner-Jones, A., Greenhough, S., A King, J., Gardner, J., Courtney, A. and Shu, W. (2013). Development of a valve-based cell printer for the formation of human embryonic stem cell spheroid aggregates. *Biofabrication*, 5(1), p. 015013.

Ferris, C., Stevens, L., Gilmore, K., Mume, E., Greguric, I., Kirchmajer, D., Wallace, G. and in het Panhuis, M. (2015). Peptide modification of purified gellan gum. *J. Mater. Chem. B*, 3(6), pp. 1106-1115.

Marga, F., Jakab, K., Khatiwala, C., Shepherd, B., Dorfman, S., Hubbard, B., Colbert, S. and Gabor, F. (2012). Toward engineering functional organ modules by additive manufacturing. *Biofabrication*, 4(2), p. 022001.

Mironov, V., Visconti, R., Kasyanov, V., Forgacs, G., Drake, C. and Markwald, R. (2009). Organ printing: Tissue spheroids as building blocks. *Biomaterials*, 30(12), pp. 2164-2174.

Pampaloni, F., Ansari, N. and Stelzer, E. (2013). High-resolution deep imaging of live cellular spheroids with light-sheet-based fluorescence microscopy. *Cell Tissue Res*, 352(1), pp. 161-177.

Tan, Y., Richards, D., Trusk, T., Visconti, R., Yost, M., Kindy, M., Drake, C., Argraves, W., Markwald, R. and Mei, Y. (2014). 3D printing facilitated scaffold-free tissue unit fabrication. *Biofabrication*, 6(2), p. 024111.

Xu, C., Zhang, M., Huang, Y., Ogale, A., Fu, J. and Markwald, R. (2014). Study of Droplet Formation Process during Drop-on-Demand Inkjetting of Living Cell-Laden Bioink. *Langmuir*, 30(30), pp. 9130-9138.

The invention claimed is:

1. A process for producing a 3D tissue culture model, the process comprising:
    (a) printing a drop of bio-ink to a substrate;
    (b) printing a drop of activator to the drop of bio-ink to form a hydrogel droplet;
    (c) repeating steps (a) and (b) in any order to form a hydrogel mold adapted to receive a drop containing cells;
    (d) printing a drop containing cells having a cell concentration of $10^7$ cells/ml or greater to the hydrogel mold; and
    (e) repeating steps (a) and (b) in any order to form a 3D tissue culture model comprising the cells wholly encapsulated in the hydrogel mold formed by the printing steps;
    wherein the printing is carried out using a bioprinter having a drop-on-demand droplet dispensing system; and wherein the 3D tissue culture model has high cell viability.

2. The process according to claim 1 wherein step (d) comprises printing a drop of cell-ink containing cells to the hydrogel mold.

3. The process according to claim 1 wherein step (d) comprises printing a drop of bio-ink containing cells and printing a drop of activator to the drop of bio-ink containing cells before step (e).

4. The process according to claim 1 wherein the substrate is suitable for containing, holding or growing cells.

5. The process according to claim 4 wherein the substrate is selected from microtitre plate of different well configurations (6, 24, 48 and 96-well), microtitre plate with coverslip bottom of different well configuration (6, 24, 48 and 96-well), fluorodish, chamber slides of different chamber configuration (1, 2, 4, 8 and 16), coverslips or microscope slides.

6. The process according to claim 1 wherein the bio-ink is compatible with cells that can form a hydrogel when exposed to a suitable activator.

7. The process according to claim 6 wherein the bio-ink comprises a synthetic macromolecule, polymer carrying amine-reactive functionalities, polymer having thiol-reactive functionalities, polymer containing fructose, sucrose or glucose functionality, non-ionic polymer, polyelectrolyte, or natural macromolecule.

8. The process according to claim 7 wherein the synthetic macromolecule is a polysaccharide, the polymer carrying amine-reactive functionalities is aldehyde, epoxy, N-hydroxysuccinimide (NHS) or 2-vinyl-4,4-dimethylazlactone (VDM), the thiol-reactive functionalities are alkenes, alkynes, azides, halogens or cyanates, the non-ionic polymer is poly(ethylene glycol) (PEG), poly(hydroxyethyl methacrylate) (PHEMA), poly(ε-caprolactone) (PCL), poly(vinyl alcohol) (PVA), poly(NIPAAM) and poly(propylene fumarate) (PPF) or derivatives, the natural macromolecule is alginate, chitosan, hyaluronic acid, agarose, glycosaminoglycan or methylcellulose, protein, gelatin, fibrin, collagen or basement membrane extract.

9. The process according to claim 1 wherein the activator is selected to form the bio-ink into a hydrogel.

10. The process according to claim 9 wherein the activator comprises inorganic salts, or photoinitiators.

11. The process according to claim 10 wherein the inorganic salts are barium chloride, calcium carbonate, calcium chloride, sodium chloride, magnesium sulphate or sodium hydroxide, the photoinitiators are 2,2-dimethoxy-2-phenylacetophenone (DMPA) and Irgacure.

12. The process according to claim 11 wherein the bio-ink is alginate and the activator is calcium chloride.

13. The process according to claim 2 wherein the cell-ink is selected from gellan gum, a neutral, highly branched, high-mass, hydrophilic polysaccharide (FICOLL), dextran, glycerol, alginate, methylcellulose or poly(vinylpyrrolidone) (PVP).

14. The process according to claim 13 wherein the cell-ink is gellan gum.

15. The process according to claim 13 wherein the cell-ink is a neutral, highly branched, high-mass, hydrophilic polysaccharide (FICOLL).

16. The process according to claim 1 further comprising incubating the cells encapsulated in the hydrogel mold at a temperature and conditions to allow or maintain cell growth or spheroid formation.

17. The process according to claim 1 wherein the 3D tissue culture model is a cellular spheroid.

18. The process according to claim 1 wherein the cell concentration is $250 \times 10^6$ cells/ml.

19. The process according to claim 1 wherein the cell concentration is up to $450 \times 10^6$ cells/ml.

20. The process according to claim 1 wherein the cell viability is 95% or greater.

* * * * *